(12) United States Patent
Hannaford et al.

(10) Patent No.: US 9,011,326 B2
(45) Date of Patent: Apr. 21, 2015

(54) SOFT TISSUE SHIELD FOR TRANS-ORBITAL SURGERY

(71) Applicant: SPIWay LLC, Carlsbad, CA (US)

(72) Inventors: Blake Hannaford, Seattle, WA (US); Randall A. Bly, Seattle, WA (US)

(73) Assignee: SPIWay LLC, Carlsbad, CA (US)

( * ) Notice: Subject to any disclaimer, the term of this patent is extended or adjusted under 35 U.S.C. 154(b) by 56 days.

(21) Appl. No.: 13/760,971

(22) Filed: Feb. 6, 2013

(65) Prior Publication Data

US 2013/0204092 A1    Aug. 8, 2013

Related U.S. Application Data

(63) Continuation-in-part of application No. 12/943,779, filed on Nov. 10, 2010, now abandoned.

(60) Provisional application No. 61/596,996, filed on Feb. 9, 2012, provisional application No. 61/261,310, filed on Nov. 14, 2009, provisional application No. 61/293,932, filed on Jan. 11, 2010, provisional application No. 61/346,476, filed on May 20, 2010.

(51) Int. Cl.
*A61B 1/32* (2006.01)
*A61B 19/00* (2006.01)
(Continued)

(52) U.S. Cl.
CPC ... *A61B 1/32* (2013.01); *A61B 1/06* (2013.01); *A61M 1/0084* (2013.01); *A61B 17/24* (2013.01); *A61B 17/3423* (2013.01); *A61B 17/3431* (2013.01); *A61B 17/3496* (2013.01); *A61B 19/00* (2013.01); *A61B 19/54* (2013.01); *A61B 2017/00849* (2013.01); *A61B 2017/00876* (2013.01); *A61B 2019/481* (2013.01); *A61B 2019/5206* (2013.01); *A61B 2217/005* (2013.01); *A61B 2217/007* (2013.01); *A61B 17/0231* (2013.01); *A61B 17/3421* (2013.01); *A61B 2017/345* (2013.01); *A61B 2019/465* (2013.01); *A61B 2017/00278* (2013.01)

(58) Field of Classification Search
CPC .......... A61B 1/32; A61B 2/00; A61B 5/6821; A61B 17/0231
USPC ............ 600/201–246; 128/898; 623/4.1–6.64
See application file for complete search history.

(56) References Cited

U.S. PATENT DOCUMENTS 3,568,678 A    3/1971    Pourquier et al.
3,664,330 A    5/1972    Deutsch
(Continued)

OTHER PUBLICATIONS

O'Brien et al. "Transorbital Approach for Occluding the Middle Cerebral Artery Without Craniectomy", Stroke. vol. 4, Mar.-Apr. 1973. pp. 201-206.*

(Continued)

*Primary Examiner* — Eduardo C Robert
*Assistant Examiner* — Jacqueline Johanas
(74) *Attorney, Agent, or Firm* — Kenneth H. Ohriner; Perkins Coie LLP

(57) ABSTRACT

A surgical shield protects collateral soft tissue from damage during a trans-orbital surgical procedure in the head of a patient. The shield may be provided as an elongated flexible sheath having one or more thin flexible sidewalls that can conform to the tissue around or bearing on the shield. Other areas or sidewalls of the shield may be thicker to better resist perforation by surgical instruments, and/or to better maintain the access lumen of pathway to the surgical site.

9 Claims, 6 Drawing Sheets

(51) Int. Cl.
  *A61B 1/06* (2006.01)
  *A61B 17/34* (2006.01)
  *A61B 17/02* (2006.01)
  *A61M 1/00* (2006.01)
  *A61B 17/24* (2006.01)
  *A61B 17/00* (2006.01)

(56) References Cited

U.S. PATENT DOCUMENTS

| | | |
|---|---|---|
| 3,867,946 A | 2/1975 | Huddy |
| 4,280,493 A | 7/1981 | Council |
| 4,312,353 A | 1/1982 | Shahbabian |
| 4,755,174 A | 7/1988 | Milewski et al. |
| 4,819,619 A | 4/1989 | Augustine et al. |
| 4,821,715 A | 4/1989 | Downing |
| 4,883,465 A | 11/1989 | Brennan |
| 4,993,406 A * | 2/1991 | Reynolds ............... 600/200 |
| 5,011,474 A | 4/1991 | Brennan |
| 5,139,510 A | 8/1992 | Goldsmith et al. |
| 5,336,163 A | 8/1994 | DeMane et al. |
| 5,400,770 A | 3/1995 | Nakao et al. |
| 5,599,284 A | 2/1997 | Shea |
| 5,601,591 A | 2/1997 | Edwards et al. |
| 5,601,594 A | 2/1997 | Best |
| 5,713,839 A | 2/1998 | Shea |
| 5,800,394 A | 9/1998 | Yoon et al. |
| 5,827,224 A | 10/1998 | Shippert |
| 5,865,728 A | 2/1999 | Moll et al. |
| 5,967,970 A | 10/1999 | Cowan et al. |
| 6,033,426 A | 3/2000 | Kaji |
| 6,083,155 A | 7/2000 | Trese |
| 6,102,928 A | 8/2000 | Bonutti |
| 6,183,493 B1 | 2/2001 | Zammit |
| 6,306,084 B1 | 10/2001 | Pinczower |
| 6,309,345 B1 | 10/2001 | Stelzer et al. |
| 6,328,753 B1 | 12/2001 | Zammit |
| 6,454,783 B1 | 9/2002 | Piskun |
| 6,607,546 B1 | 8/2003 | Murken |
| 7,100,612 B2 | 9/2006 | Dunlap |
| 7,361,168 B2 | 4/2008 | Makower et al. |
| 7,410,480 B2 | 8/2008 | Muni et al. |
| 7,520,876 B2 | 4/2009 | Ressemann et al. |
| 7,654,997 B2 | 2/2010 | Makower et al. |
| 7,678,099 B2 | 3/2010 | Ressemann et al. |
| 7,720,521 B2 | 5/2010 | Chang et al. |
| 7,727,186 B2 | 6/2010 | Makower et al. |
| 7,730,888 B2 | 6/2010 | Dunlap |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,799,337 B2 | 9/2010 | Levin |
| 7,918,871 B2 | 4/2011 | Truitt et al. |
| 8,409,083 B2 | 4/2013 | Mangiardi |
| 2002/0013511 A1 | 1/2002 | Ailinger et al. |
| 2003/0014076 A1 | 1/2003 | Mollenauer et al. |
| 2003/0154986 A1 | 8/2003 | Fariss et al. |
| 2004/0138525 A1 | 7/2004 | Saadat et al. |
| 2004/0210114 A1 | 10/2004 | Simon |
| 2004/0230100 A1 | 11/2004 | Shluzas |
| 2004/0243172 A1 | 12/2004 | Hogle |
| 2005/0059960 A1 | 3/2005 | Simaan et al. |
| 2005/0075540 A1 | 4/2005 | Shluzas et al. |
| 2005/0165366 A1 | 7/2005 | Brustad et al. |
| 2005/0240147 A1 | 10/2005 | Makower et al. |
| 2006/0004323 A1 | 1/2006 | Chang et al. |
| 2006/0173407 A1 | 8/2006 | Shaughnessy et al. |
| 2006/0200003 A1 | 9/2006 | Youssef |
| 2006/0287583 A1 | 12/2006 | Mangiardi |
| 2007/0005094 A1 | 1/2007 | Eaton et al. |
| 2007/0016174 A1 | 1/2007 | Millman et al. |
| 2007/0021773 A1 | 1/2007 | Nolte |
| 2007/0100370 A1 | 5/2007 | Hogle |
| 2007/0191876 A1 | 8/2007 | Dubrul et al. |
| 2007/0203474 A1 | 8/2007 | Ryan et al. |
| 2007/0219575 A1 | 9/2007 | Mejia |
| 2007/0225568 A1 | 9/2007 | Colleran |
| 2007/0277831 A1 | 12/2007 | Luhrs |
| 2007/0293726 A1 | 12/2007 | Goldfarb et al. |
| 2007/0299314 A1 | 12/2007 | Bertolero et al. |
| 2008/0027464 A1 | 1/2008 | Moll et al. |
| 2008/0045803 A1 | 2/2008 | Williams et al. |
| 2008/0058590 A1 | 3/2008 | Saadat et al. |
| 2008/0065105 A1 | 3/2008 | Larkin et al. |
| 2008/0065108 A1 | 3/2008 | Diolaiti |
| 2008/0071288 A1 | 3/2008 | Larkin et al. |
| 2008/0097514 A1 | 4/2008 | Chang et al. |
| 2008/0097516 A1 | 4/2008 | Chang et al. |
| 2008/0109026 A1 | 5/2008 | Kassam |
| 2008/0132938 A1 | 6/2008 | Chang et al. |
| 2008/0188868 A1 | 8/2008 | Weitzner et al. |
| 2008/0234550 A1 | 9/2008 | Hawkes et al. |
| 2008/0234720 A1 * | 9/2008 | Chang et al. ............... 606/196 |
| 2008/0243064 A1 | 10/2008 | Stahler et al. |
| 2008/0255519 A1 | 10/2008 | Piskun et al. |
| 2008/0260732 A1 * | 10/2008 | Ramakrishnan et al. .. 424/133.1 |
| 2008/0275483 A1 | 11/2008 | Makower et al. |
| 2009/0010991 A1 | 1/2009 | Prabhu et al. |
| 2009/0054728 A1 | 2/2009 | Trusty |
| 2009/0062927 A1 | 3/2009 | Marten et al. |
| 2009/0137952 A1 | 5/2009 | Ramanurthy et al. |
| 2009/0312745 A1 | 12/2009 | Goldfarb et al. |
| 2010/0030031 A1 | 2/2010 | Goldfarb et al. |
| 2010/0076555 A1 | 3/2010 | Marten et al. |
| 2010/0100181 A1 | 4/2010 | Makower et al. |
| 2010/0145147 A1 | 6/2010 | Pinsky et al. |
| 2010/0174149 A1 | 7/2010 | Moll et al. |
| 2010/0174308 A1 | 7/2010 | Chang et al. |
| 2010/0179537 A1 | 7/2010 | Rashidi |
| 2010/0211181 A1 | 8/2010 | Prabhu et al. |
| 2010/0211186 A1 * | 8/2010 | Senders et al. ............... 623/24 |
| 2010/0228227 A1 | 9/2010 | Krespi et al. |
| 2010/0249523 A1 | 9/2010 | Spiegal et al. |
| 2010/0298862 A1 | 11/2010 | Chang et al. |
| 2010/0331777 A1 | 12/2010 | Danielsson |
| 2011/0004194 A1 | 1/2011 | Eaton et al. |
| 2011/0118551 A1 | 5/2011 | Ciporen et al. |
| 2011/0125092 A1 | 5/2011 | Hepworth et al. |
| 2012/0149990 A1 * | 6/2012 | Buehler et al. ............... 600/210 |
| 2013/0092173 A1 | 4/2013 | Alexander et al. |

OTHER PUBLICATIONS

Cockerham et al. "Surgery for Orbital Tumors. Part II: Transorbital Approaches", Neurosurg Focus. 2001; 10(5).*
Ciporen et al. "Multiportal Endoscopic Approaches to the Central Skull Base: A Cadaveric Study", World Neurosurgery. 73(6), Jun. 2010, pp. 705-712.*
Moe et al. "Transorbital Neuroendoscopic Surgery", Neurosurgery. Sep. 2010; 67(3 Suppl Operative), pp. 16-28.*
International Search Report dated Jul. 28, 2011 in PCT Application No. WO11/060125 A3.

* cited by examiner

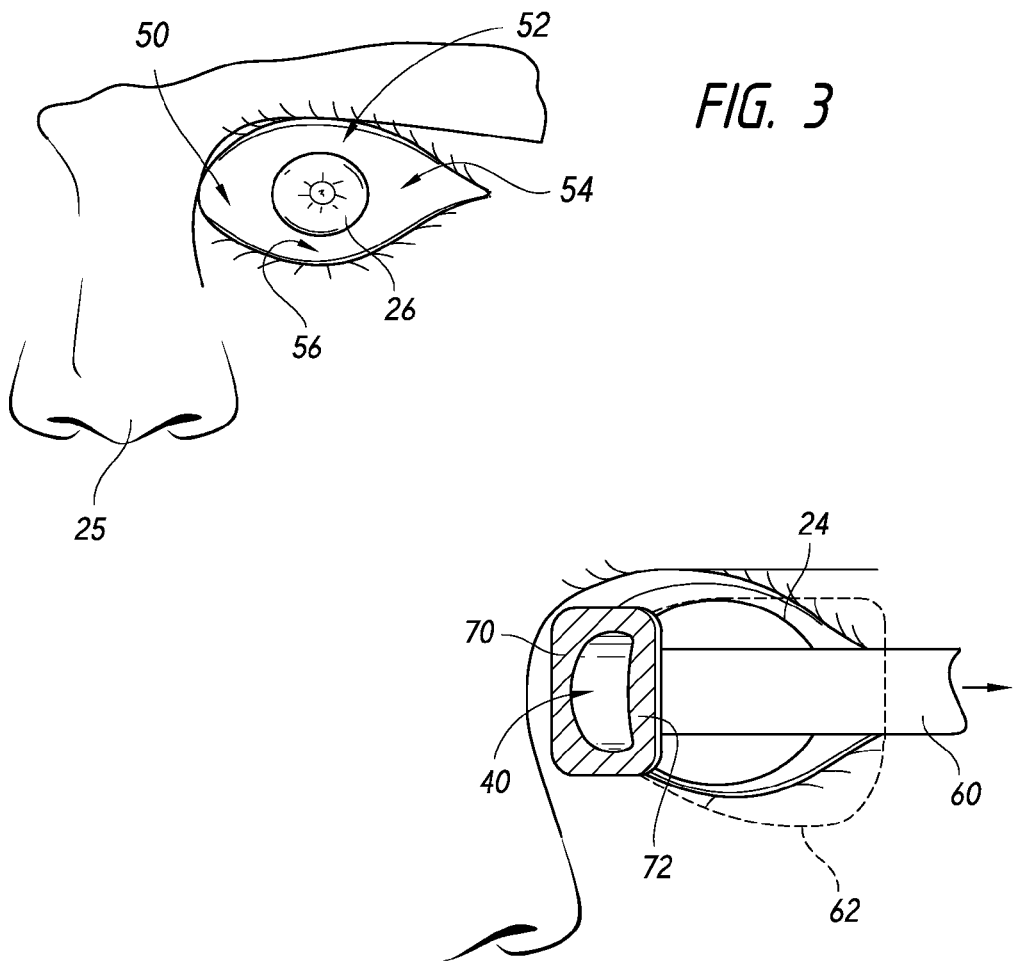
FIG. 3
FIG. 4
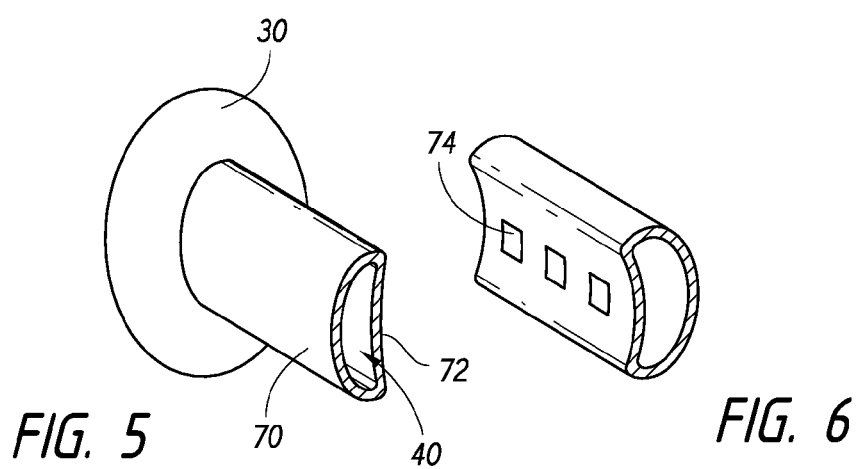
FIG. 5
FIG. 6

SOFT TISSUE SHIELD FOR TRANS-ORBITAL SURGERY

PRIORITY CLAIM

This Application claims priority to U.S. Provisional Patent Application No. 61/596,996 filed Feb. 9, 2012. This Application is also a Continuation-in-Part of U.S. patent application Ser. No. 12/943,779 filed on Nov. 10, 2010, which claims priority to U.S. Provisional Patent Application Nos. 61/261,310, filed Nov. 14, 2009; 61/293,932, filed Jan. 11, 2010; and 61/346,476, filed May 20, 2010, each incorporated herein by reference. U.S. patent application Ser. No. 13/369,952 filed on Feb. 9, 2012 is also incorporated herein by reference.

BACKGROUND OF THE INVENTION

Endoscopic surgery within the head is a common procedure in neurological surgery and otolaryngology. Advantages to endoscopic surgery of the head include avoiding large cranial incisions and brain retraction. Endoscopic, surgery of the head can provide the surgeon with a better view because the camera of the endoscope is brought directly to the surgical site.

During this type of surgery using a trans-orbital approach, there tends to be some local trauma to the orbital and peri-orbital tissue. This surgical pathway trauma can add to the trauma of the procedure and prolong the patient's recovery time. In addition, there is frequent and persistent "run down" of blood and soiled irrigation fluid that obscures the view of the endoscope. This leads to the constant need for irrigation and suction of these liquids, as well as removal, cleaning and replacement of the endoscope. This can occur many times during a single procedure, making the cleaning and clearing of the endoscope time consuming.

Accessing the surgical site through any route, but especially through the trans-orbital route, may require the surgeon to travel around or through internal tissue structures within the head, often using multiple instruments. When an instrument needs to be substituted, or an endoscope needs to be cleaned, the surrounding tissues are again put at risk as the instruments are removed and reinserted.

Therefore, there is a need to reduce or eliminate these problems encountered in endoscopic trans-orbital surgery.

SUMMARY OF THE INVENTION

A surgical shield protects collateral soft tissue from damage during an intra-orbital surgical procedure in the head of a patient. The shield may be provided as an elongated flexible sheath. The shield may have one or more thin flexible sidewalls that can conform to the tissue around or bearing on the shield. Other areas or sidewalls of the shield may be thicker to better resist perforation by surgical instruments, and/or to better maintain the access lumen of pathway to the surgical site.

Other features and advantages will become apparent from the following detailed description of examples of how the invention may be designed and used. The invention resides as well in sub-combinations of the elements and method steps described.

BRIEF DESCRIPTION OF THE DRAWINGS

In the drawings, the same element number indicates the same element in each of the views:

FIG. 3 is a front view diagram slowing trans-orbital positions where the shield may be placed.

FIG. 4 is front view diagram illustrating placement of the shield.

FIG. 5 is rear perspective view of an alternative shield design.

FIG. 6 is a front section view of another alternative shield design.

DETAILED DESCRIPTION

Figure 1:
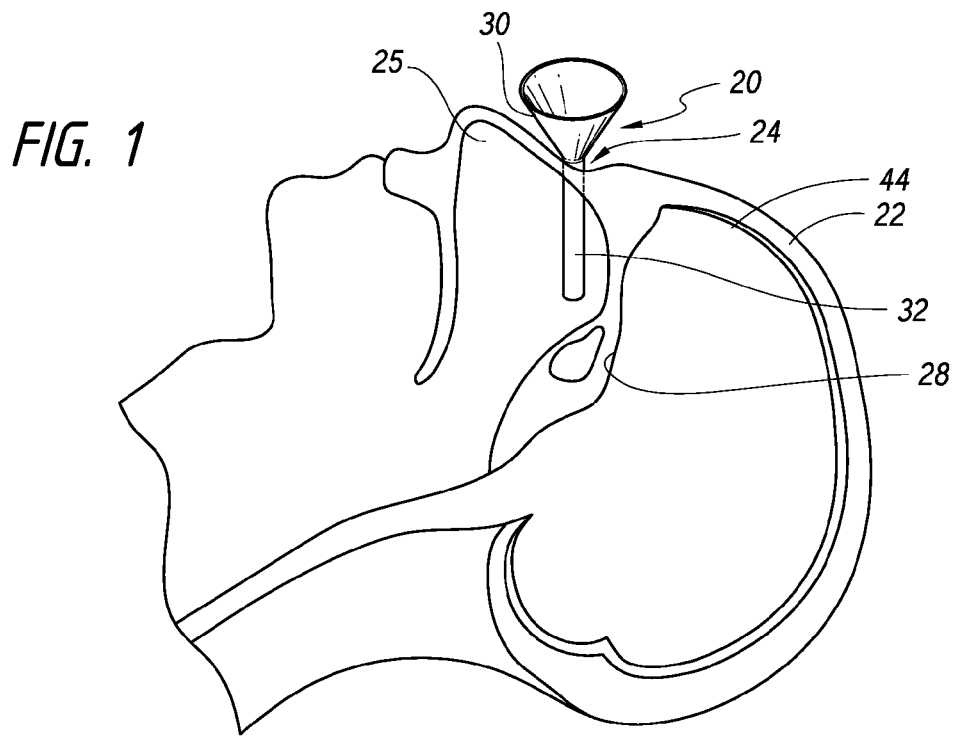
FIG. 1 is section view of a human head and surgical shield deployed trans-orbitally.
Figure 2:
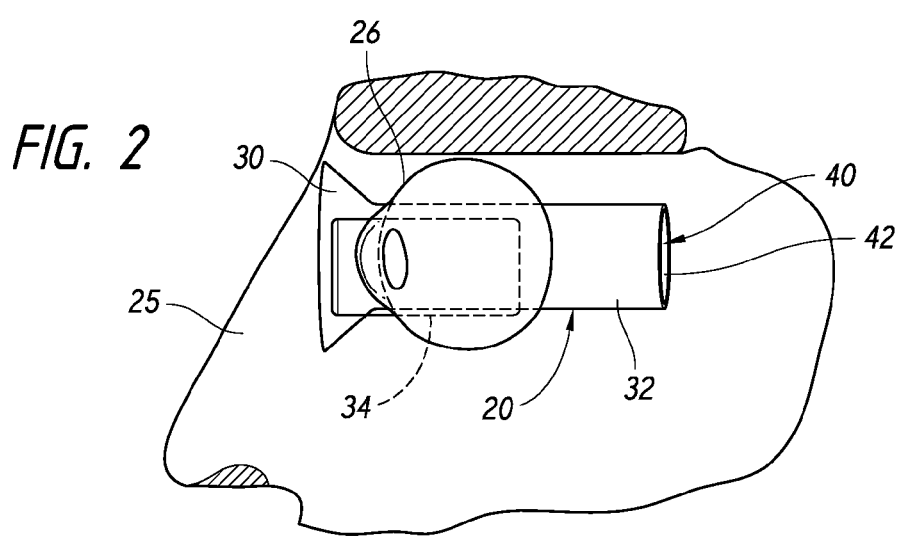
FIG. 2 is a section view of the shield of FIG. 1 showing additional elements.

Turning now to the drawings, as shown in FIGS. 1 and 2, a shield 20 is shown in use during a trans-orbital approach to surgery within the head 22. The shield 20 has an outwardly flared or conical proximal end 30 and a smaller diameter distal end 32. A main channel or lumen 40 extends through the shield 20, to allow surgical instruments be moved to and withdrawn from the surgical site 28, while limiting or avoiding collateral damage to surrounding tissue.

The flare or conical shape of the proximal end 30 of the shield 20 allows for easy insertion and re-insertion of instruments/endoscopes through the main channel 40 leading to the surgical site 28. The inside surfaces 42 of the shield 20 are smooth to allow surgical instruments to slide easily through the main channel 40 and avoid piercing the shield and the collateral soft tissue with the instruments. The inside surfaces 42 may be coated with a low friction coating such as hyaluronan, or glycerin. This makes the inner surface a low friction surface to assist in easier insertion of instruments into the shield 18

FIGS. 2 and 4 show an example of placing the shield 20 by moving the eye 26 using a malleable retractor 60, to retract the orbit and reveal the surgical pathway to the surgical site 28. In FIGS. 1 and 2, the eye 26 is temporarily displaced and the distal end 32 of the shield 20 is inserted through the orbital opening 24 in the skull 44. As shown in FIG. 4, the shield 20 sits within and conforms to the surrounding tissue. An extension 34 at the proximal end of the shield may optionally drape over the retractor 60 and, in effect, widen the shield 20 to provide for easier insertion and reinsertion of instruments. If used, the extension 34 may also help to protect the orbit, sclera and cornea from accidental contact with fluids or small dropped objects. If used, the extension 34 may be made as a lisp or addition to the proximal end 30 of the shield 20.

Referring momentarily to FIG. 4, a similar extension 62 shown in dotted lines is located at the temporal portion of the shield, and acts as external eye cover. The extension may be formed by extending or increasing the size of the proximal end 30. The extension may be held in place by gravity if the patient is in a supine position, or it may held in place by adhesive, tape or a suture if the patient is in another position. Standard ophthalmic ointment, which is routinely applied to the cornea in orbital surgery, may be used as an adhesive to hold the extension in place over the cornea. Common ointments, such as erythromycin ophthalmic ointment, are thick and viscous, and may be used to hold the extension in place, and not rub or cause abrasions to the cornea.

FIG. 4 shows the shield 20 placed at medial orbit 50. This is also referred to as the precaruncular surgical approach. As shown FIG. 3, the shield 20 may alternatively be placed at other positions as well. These include the superior orbit 52, also referred to as the superior lid crease surgical approach; the lateral or temporal orbit 54, also referred to as the lateral retrocanthal surgical approach; and the inferior orbit 56, also referred to as the preseptal surgical approach. Each portal permits access to different locations in the peri-orbital region, orbital apex, and skull base. These can be individual approaches, or can be combined in multiportal approaches with other portals, such as transnasal or transoral.

Figure 11:
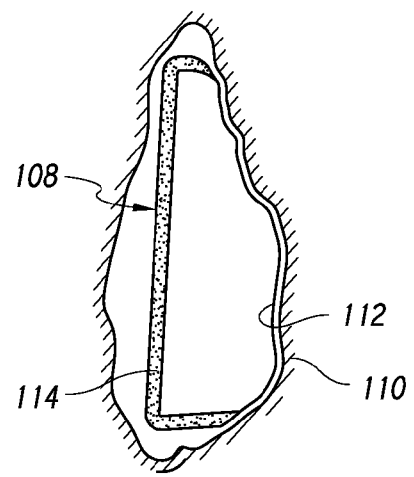
FIG. 11 is a schematic section showing a shield having selected wall thicknesses.

As shown in FIG. 5, the shield 20 may have walls of varying thickness and flexibility. In this example, the outer wall 72 of the shield is thin and highly flexible, to comply with surrounding tissue. The inner wall 70 may be thicker and stiffer, to provide column strength to the shield. This allows the shield to resist axial compression forces during insertion, to better resist buckling, without using an auxiliary supporting device. In the design shown, with the shield integrally molded of medical grade plastic or rubber, the outer wall may be 0.005 to 0.04 inches thick, while the inner wall 70 may be 0.03 to 0.07 thick. The shield may alternatively be formed of, for example, latex rubber, silicone rubber, latex or polymeric silicone substances, or other flexible polymer materials and/or other biocompatible elastic material The wall thicknesses may also be selected, at least in part, based on the anticipated resistance to puncture needed for specific applications. In some procedures for example, the distal ends of the instruments passed through the main channel 40 of the shield 20 may tend to contact only the inner wall, and not the outer wall, due to the position of the shield and the patient's head, as well as the size and shape of the instruments. In a shield 20 for use in this type of application, the inner wall 114 may be substantially thicker than the outer wall 112. FIG. 11 illustrates a thin outer wall 112 of a similar shield 108 complying against a tissue surface 110.

The shield 20 may also be shaped based on the intended surgical approach. For example, as shown in FIGS. 5 and 6, the inner wall 70 may be concave and the outer wall may be convex. During trans-orbital use, the outer wall 72 may hear against the eye. To monitor pressure exerted on the eye during surgery, one or more pressure sensors 74 may be attached to or built, into the shield 20, as shown in FIG. 6. Wire leads from the pressure sensors run forward and out from the proximal end 30 of the shield, to allow the surgeon to monitor pressure over time and avoid over pressuring the eye.

The pressure sensors 74 may be used in other applications to measure pressure on other tissue or structures, such as the orbit or the brain. The orientation of the shield may be adjusted so that an array of pressure sensors is positioned up against the structure of interest. Using real-time feedback from the pressure sensors, the surgeon can adjust the degree of retraction, or make other changes, to minimize tissue injury.

Figure 7:
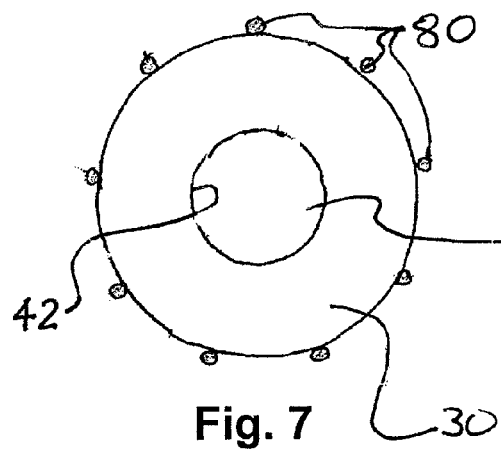
FIG. 7 is a rear view of a shield having an irrigation system or suction system.
Figure 8:
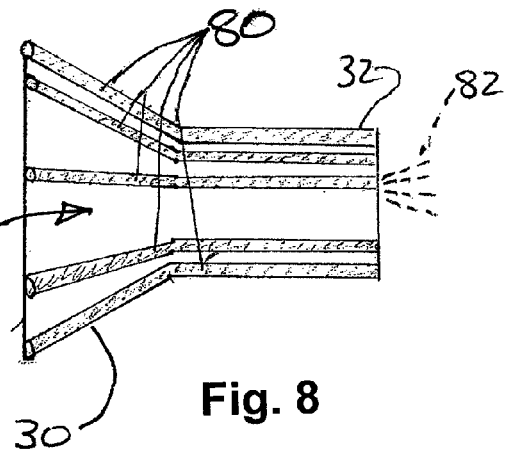
FIG. 8 is a side view of the shield shown in FIG. 7.

Turning now to FIGS. 7 and 8, in an alternative design, secondary channels or ducts 80 are fitted alongside and/or within the walls of the shield 20. The channels 80 may run for entire length, or for a fraction of the length, of the shield. Catheters, fiberoptic fibers, and wires may be passed through the channels 80. A catheter in a channel can be used to provide suction or irrigation or pressure measurements. Wires in the channels may be used to connect to pressure sensors 74, or to power lighting elements, such as LEDs in the shield. Fiber optic lines may also optionally be provided to project light out from the distal end of the shield, and to transmit back images.

Figure 10:
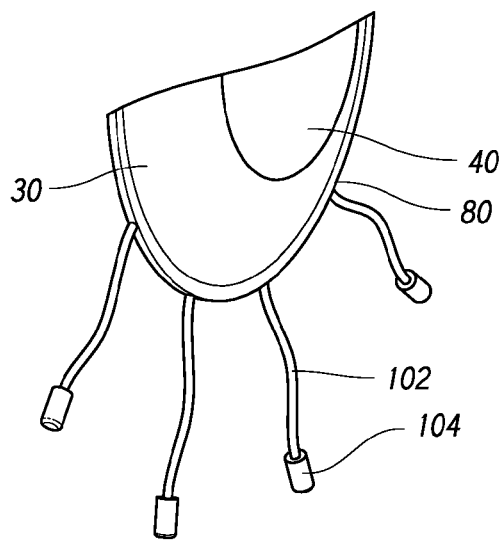
FIG. 10 is a rear view of a shield having multiple separate connection fittings for irrigation or suction.

FIG. 10 shows one option for connecting the channels 80 or wires on the shield 20 with irrigation/suction or electrical equipment. Here, extension tubes or wires 102 separately connect into each channel and extend radially outward. A fluid coupler 104, such as a Luer lock, is attached onto the ends of the extension tubes 102. An electrical connector is similarly attached to wire extensions. Multiple channels could be used in combination simultaneously.

The channels themselves may act as catheters, when connected directly to a suction or irrigation device. As shown in FIG. 8, generally the channels 80 extend to the distal end 32 of the shield. This allows irrigation fluid, such as fluid 82 in FIG. 8, to be supplied to the surgical site, or to instruments, such as the lens of an endoscope, adjacent to the surgical site. Similarly, channels at that the distal end of the shield used for suction can evacuate fluid from areas near the surgical site.

In some designs, one or more channels 80 may stop short of the distal end of the shield, and have spaced apart openings that may be used to continuously or intermittently rinse and/or evacuate the main channel 40. LEDs or other lighting elements may also be provided to the inside of the shield. If the shield is made of a transparent or translucent material, the tissues surrounding the shield may also be illuminated by the lighting elements. It is also possible to position lighting elements to direct light outwardly from the external surfaces of the shield walls, rather than internally The channels 80 may be radially spaced apart around the circumference of the shield, so that regardless of the orientation of the shield, there will always be channels that are the top and bottom of the shield with respect to gravity. For example, an irrigation portal may be located at the top portal for a given orientation, with a gravity-dependent channel located at the bottom, or 180 degrees opposite, used for suction. Multiple fluid channels may be used in combination simultaneously.

Figure 9:
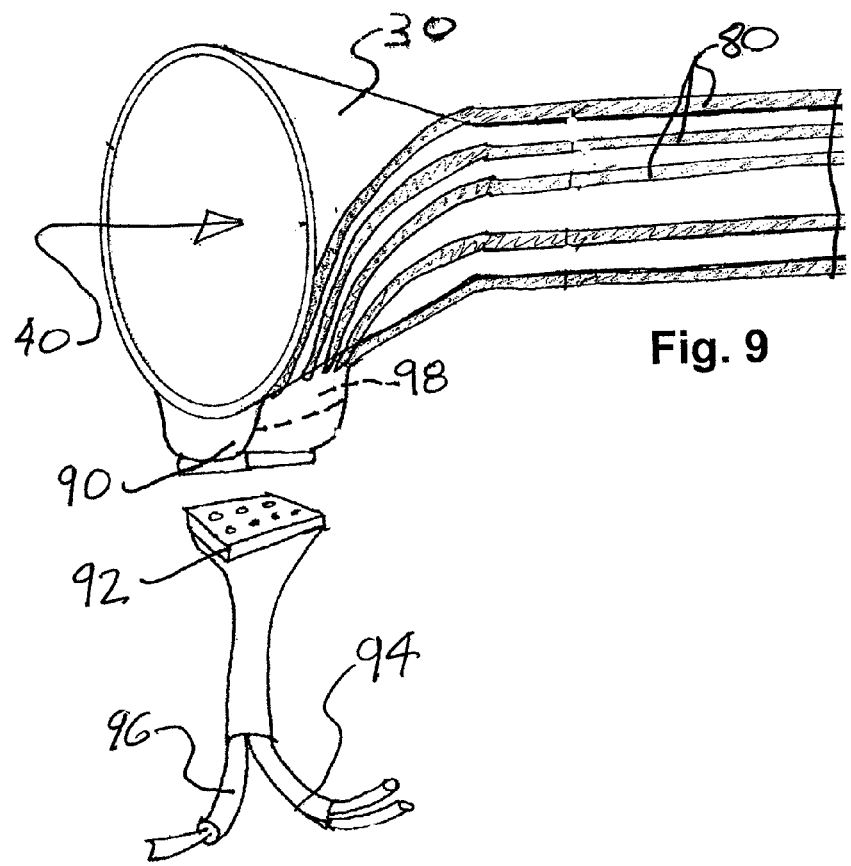
FIG. 9 is a perspective view of a shield having an irrigation/suction fitting.

As Shown in FIG. 9, for shields having channels 80, or Wires for electrical connections, a multi-channel connector block 90 may be used, instead of individual tubes or wire leads connecting the shield to irrigation, suction or electrical equipment. The multi-channel connector block 90 can be used to organize suction and irrigation channels in a convenient array to permit quick connection of multiple channels simultaneously. A multi-channel connector plug 92 connects to the block 90. The multi-channel connector plug 92 then leads to multiple options for each channel. These options include suction, irrigation, and electrical connections for illuminating the inside of the shield via lighting elements but into the walls of the shield 20, of connecting to other electrical components on or in the shield 20, such as the pressure sensors 74.

The organization of the array of tubes and/or wires may position the suction/irrigation channels based on the orientation of be shield with respect to gravity. As shown in FIG. 9, the connector block 90 extends radially outwardly at the proximal end of the shield, to void obstructing the main channel 40. A manifold 98 may optionally be provided on the shield, or in the connector block 90, to provide a single common distribution or collection path for irrigation or suction.

Figure 12:
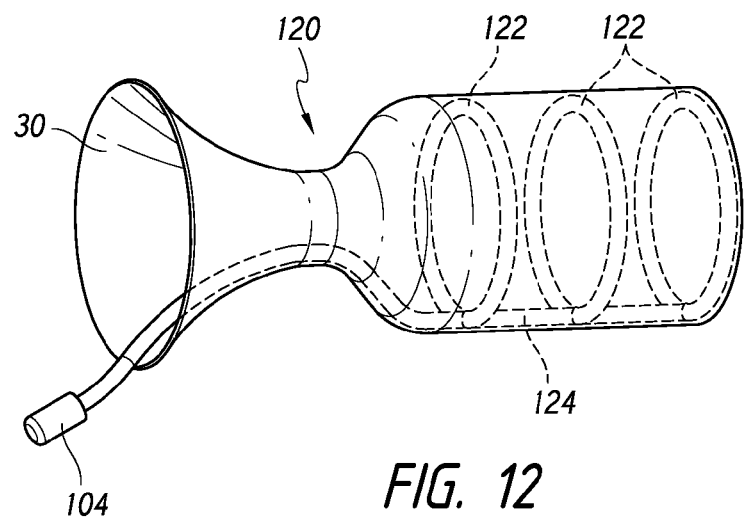
FIG. 12 is a perspective view of a shield having inflatable elements.

As shown in FIG. 12, in an alternative shield 120, inflatable ribs 122 may be used to open up and maintain the main channel 40 through the shield. In this design, when inflated, the ribs 122 hold the shield open. The ribs may act like batons in stenting open the main channel 40. A one-way valve fluid/air coupler 104 may be used to provide variable pressure to the ribs. A syringe may be connected to the coupler 104 to inflate the ribs 122 to a desired level of pressure of air or fluid, and the syringe then removed. The coupler maintains the pressure until the syringe is connected again to further adjust the pressure, or release the pressure altogether.

Figure 13:
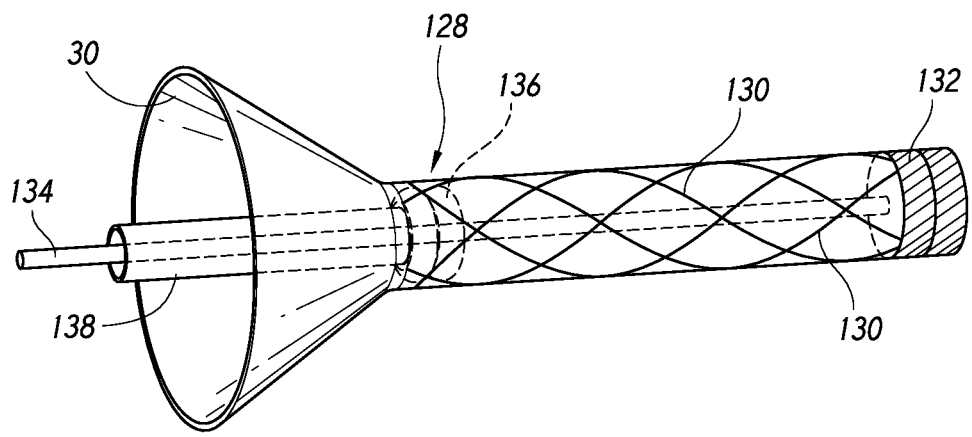
FIG. 13 is a side view of a shield in an insertion configuration.
Figure 14:
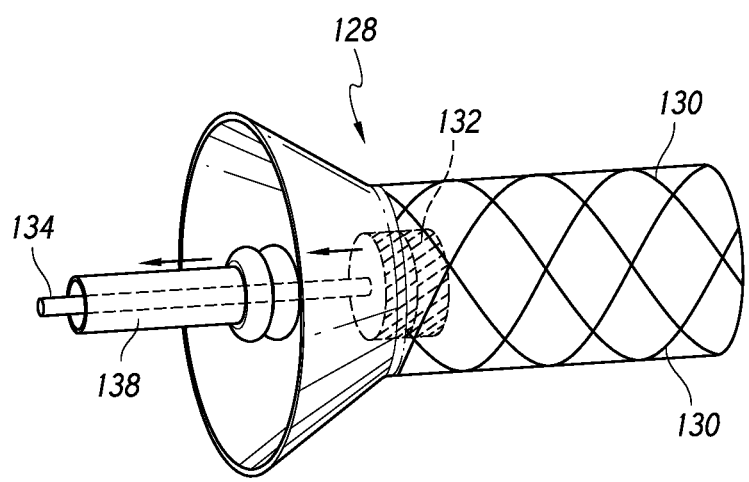
FIG. 14 is a side view of the shield shown in FIG. 13, with the shield now in a deployed or in-use configuration.

FIGS. 13 and 14 show another design for a shield 128 using helical elastic elements 130 that change the diameter of the central and distal sections of the shield when their length is adjusted. A distal end holder 132 is connected to a distal end deployment rod 134. A proximal end deployment rod 138 is connected to a proximal end holder 136, and is co centric to the distal end deployment rod 134. Working together, these elements change length in order to widen and narrow the diameter of the shield, from the configuration shown in FIG. 13, to the configuration shown in FIG. 14. For many surgical situations, the shield 128 in the narrow diameter configuration of FIG. 13 is inserted through a relatively narrower opening, such as a trans-orbital opening. The shield 128 is then reconfigured into a shorter and larger diameter configuration as shown in FIG. 14, to provide a larger main channel 40.

Figure 15:
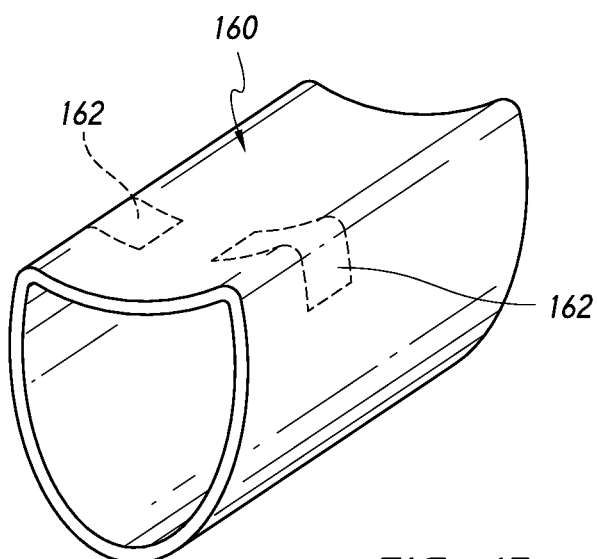
FIG. 15 is rear perspective view of a shield having elastic or spring elements to assist in deploying the shield.
Figure 16:
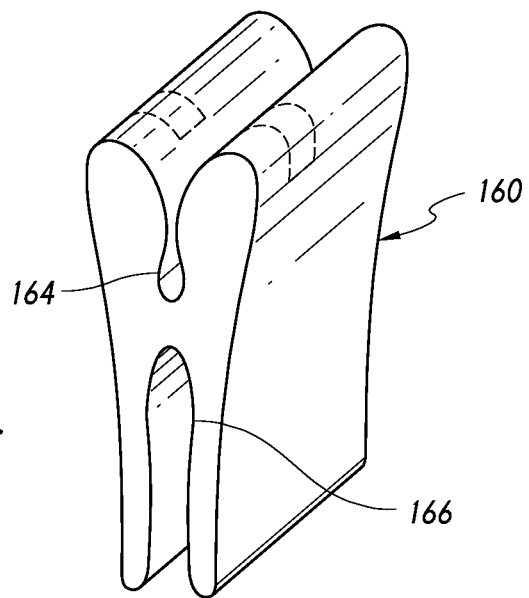
FIG. 16 is a perspective view of the shield shown in FIG. 16 in an invaginated configuration.

Referring now to FIG. 15, a shield 160 may have thin walls and thick walls. In some cases, one or more of the walls 164, 166 may deflect or collapse inwardly, tending to close of the main channel 40. Springs 162 may be attached to, or embedded into, the walls at locations where collapse is most likely to occur, for example at the junction between thick and thin wall sections, as shown in FIG. 15. The shield 160 may be folded for insertion, as shown in FIG. 16, to reduce its envelope size. The envelope size or diameter refers to the maximum dimension of any cross section of the shield. The envelope size hence determines the minimum opening that the shield can fit through, without folding or otherwise compacting the shield. After the shield is in place and the shield is released, the springs assist in restoring the shield to its unfolded configuration and re-opening the central channel.

In some designs, the shield may automatically expand or unfurl from the rolled up or compressed position into a fully deployed position, via a natural spring force of the shield material. The surgeon may assist in the deployment, if necessary, by selectively pushing on the shield using a surgical tool.

The shields may be provided in varying lengths and diameters, with the surgeon selecting a specific size based on the specific anatomy of the patient, or other factors. The shields may also be used in methods where they are cut to a desired length by the surgeon, prior to placement. Scale markings may be printed or molded onto the shields to assist the surgeon in cutting the shield to the desired size. In some cases, it may also be useful to out the conical end 30 to a desired length and/or shape, before or after the shield placed. The diameter of proximal end of the shield may be made large enough so that a surgeon may feed instruments into the shield while watching the endoscope display. For this purpose, the diameter of the proximal end may be 2, 3, or 4 inches in diameter.

The shields may include radio opaque material, in the form of one or more strips, wires, dots, or other shapes of metal material. A radiolucent strip embedded in the walls of the shield allows for confirmation of placement with fluoroscopy, and it also may be registered and integrated with surgical navigation. Multiple strips may make registration and/or orientation more convenient. The strip could be embedded in any wall of the shield.

From the foregoing, it can be seen that the invention provides surgical shields that protect collateral soft tissue from damage during a surgical procedures, and also define and maintain the access pathway to the surgical site. The shields may incorporate many different functions to assist in the surgery including irrigation, suction, and light projection.

Thus, various designs and methods have been shown and described. Many changes and substitutions can of course be made within the spirit and scope of the invention. The invention, therefore, should not be limited, except by the following claims and their equivalents.

The invention claimed is:

1. A method of performing a trans-orbital surgical procedure in the head of a patient, comprising:
retracting the eye;
moving a distal end of a shield through the orbital opening;
securing the shield in position, with a proximal end of the shield external to the head of the patient, and with shield having at least one flexible sidewall substantially conforming to tissue around the distal end of the shield;
moving a distal end of a surgical instrument through the shield and into the head of the patient;
performing a surgical procedure ire the head of the patient using the surgical instrument; and
removing the shield from the orbital opening.

2. The method of claim 1 further comprising reducing the envelope size of the distal end of the shield before moving it through the orbital opening.

3. The method of claim 2 further comprising reducing the envelope size of the distal end of the shield by forming one or more invaginations in the shield.

4. The method of claim 2 further comprising reducing, the envelope size of the distal end of the shield by stretching the distal end of the shield into an elongated configuration.

5. The method of claim 1 with the shield having a first wall having a thickness less than a second wall, and further comprising orienting the shield with the first wall against the eye.

6. The method of claim 1 further comprising measuring pressure exerted on surrounding tissue by the shield.

7. The method of claim 1 further comprising supplying an irrigation liquid to the surgical site through irrigation ducts in the shield.

8. The method of claim 1 further composing removing liquid from the surgical site through suction ducts in the shield.

9. The method of claim 1 further comprising illuminating a main channel through the shield via lighting elements on the shield.

\* \* \* \* \*